United States Patent [19]

Carini

[11] Patent Number: 5,264,581
[45] Date of Patent: Nov. 23, 1993

[54] RADIOIODINATED ANGIOTENSIN RECEPTOR ANTAGONISTS

[75] Inventor: David J. Carini, Wilmington, Del.

[73] Assignee: E. I. Du Pont de Nemours and Company, Wilmington, Del.

[21] Appl. No.: 891,546

[22] Filed: May 29, 1992

[51] Int. Cl.$^5$ .............. C07D 403/10; C07D 233/64
[52] U.S. Cl. .............................. 548/253; 548/312.7; 548/323.1
[58] Field of Search ............... 548/253, 312.7, 323.1

[56] References Cited

PUBLICATIONS

Chiu et al., "Identification of Angiotensin II Receptor Subtypes", Biochem. and Biophys. Research Commun., vol. 165: pp. 196–203 (1989).

Chiu et al., "[$^3$H]DUP 753, A Highly Potent and Specific Radioligand . . . ", Biochem. and Biophys. Research Commun., vol. 172: pp. 1195–1202 (1990).

*Primary Examiner*—David B. Springer

[57] ABSTRACT

Disclosed are novel radioiodinated imidazole Angiotensin II antagonists that are useful radioligands. An illustrative compound of this novel class of compounds is 4-chloro-N-[2-[4-hydroxy-3-(iodo-125I)phenyl]ethyl]-2-propyl-1-[[2'-(tetrazol-5-yl)biphenyl-4-yl]methyl]imidazole-5-carboxamide.

7 Claims, No Drawings

RADIOIODINATED ANGIOTENSIN RECEPTOR ANTAGONISTS

FIELD OF THE INVENTION

This invention relates to radioiodinated imidazole Angiotensin II antagonists which are useful as radioligands.

BACKGROUND OF THE INVENTION

Angiotensin II (AII) is an octapeptide hormone which is a component of the renin-angiotensin system. Angiotensin II mediates a number of physiological responses in several tissues including the constriction of vascular smooth muscle, the synthesis and secretion of aldosterone by the adrenal cortex, and retention of salt and water by the kidney (W. W. Douglas, "Polypeptides—Angiotensin Plasma Kinins, and Others", in The Pharmacological Basis of Therapeutics (A. G. Gilman et al., eds.) MacMillan, New York, 640-643 (1985).

Radioligand binding studies have shown that Angiotensin II receptors exist in at least two subtypes: $AT_1$ and $AT_2$ (A. T. Chiu et al., Biochem. Biophys. Res. Commun. 165:196-203 (1989). The $AT_1$ subtype is coupled to calcium/inositol phosphate metabolism, and is responsible for the major cardiovascular effects of Angiotensin II (A. T. Chiu et al., J. Pharmacol. Exp. Ther. 252:711-718 (1990)); (D. T. Dudley et al., Mol. Pharmacol. 38:370-377 (1990)). Drugs that block the $AT_1$ receptor therefore show great potential as antihypertensive agents.

A radiotritiated imidazole [$^3$H] DuP 753 (A. T. Chiu et al., Biochem. Biophys. Res. Commun., 172:1195-1202 (1990)) has been used to characterize the $AT_1$ receptor in rat adrenal cortical membranes and other tissues such as rat aortic smooth muscle cells. Discovering other radioligands, especially those with high specific activity, would be highly desirable. Such new radioligands would be useful tools in exploring and further characterizing receptors in the angiotensin system such as those of the $AT_1$ type. Radioiodinated peptides such as [$^{125}$I]AII are known (A. T. Chiu et al., Biochem. Biophys. Res. Commun. 165:196-203 (1989)), but not the radioiodinated imidazoles which are the newly discovered non-peptide AII receptor antagonists of the present invention.

Imidazole AII antagonists such as DuP 753 have been disclosed in EPO 0,253,310 (published Jan. 20, 1988) and EPO 0,324,377 (published Jul. 19, 1989). The radioiodinated compounds of the present invention or their use are not disclosed or suggested by any of the above references.

SUMMARY OF THE INVENTION

According to the present invention there are provided novel compounds of formula (I) which are radioiodinated angiotensin II antagonists:

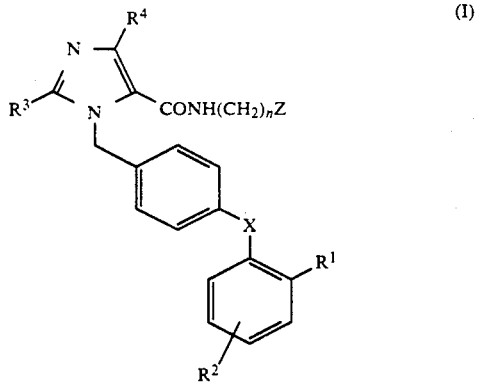

wherein
$R^1$ is $CO_2H$; $NHSO_2CF_3$; $SO_3H$; or

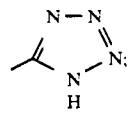

$R^2$ is H, alkyl of 1 to 4 carbon atoms, halogen, or alkoxy of 1 to 4 carbon atoms;
$R^3$ is alkyl, alkenyl, or alkynyl of 2 to 7 carbon atoms;
$R^4$ is H, Cl, Br, I; alkyl of 1 to 4 carbon atoms; $C_vF_{2v+1}$, where v=1-3;
X is a carbon-carbon single bond, —CO—, —O—, —S—, or —CONH—;
Z is

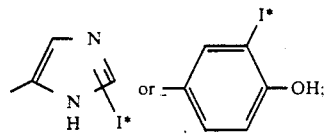

I* is I-123, I-125, or I-131; and
n is 1-3 and pharmaceutically acceptable salts thereof.

Preferred compounds of the above formula are those in which
$R^1$ is

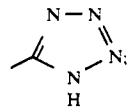

$R^2$ is H; and
X is a carbon-carbon single bond.

Illustrative of preferred compounds of the invention are the following:
4-chloro-N-[2-[4-hydroxy-3-(iodo-125I)phenyl]ethyl]-2-propyl-1-[[2'-(tetrazol-5-yl)biphenyl-4-yl]methyl]imidazole-5-carboxamide
4-chloro-N-[2-[4-hydroxy-3-(iodo-123I)phenyl]ethyl]-2-propyl-1-[[2'-(tetrazol-5-yl)biphenyl-4-yl]methyl]imidazole-5-carboxamide
4-chloro-N-[2-[4-hydroxy-3-(iodo-131I)phenyl]ethyl]-2-propyl-1-[[2'-(tetrazol-5-yl)biphenyl-4-yl]methyl]imidazole-5-carboxamide 4-ethyl-N-[2-[4-hydroxy-3-(iodo-125I)phenyl]ethyl]-2-propyl-1-[[2'-(tetrazol-5-yl)biphenyl-4-yl]methyl]imidazole-5-carboxamide the presence of an oxidant such as chloramine-T (see: Nature, 194:495 (1962)) to afford the radiolabeled derivatives formula (I).

SCHEME I

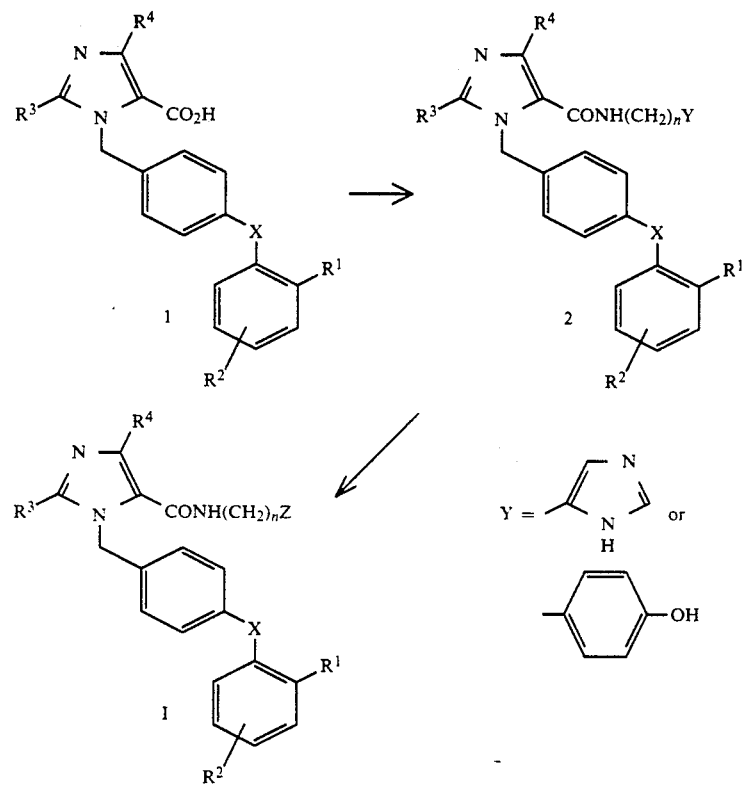

4-chloro-N-[2-[2-(iodo-125I)imidazol-4(5)-yl]ethyl]-2-propyl-1-[[2'-(tetrazol-5-yl)biphenyl-4-yl]methyl]imidazole-5-carboxamide

DETAILED DESCRIPTION OF THE INVENTION

The compounds of this invention may be prepared as shown is Scheme I. The starting imidazole-5-carboxylic acids 1 are prepared as described in EPO 0 324 377, supra. The acids 1 are activated for coupling employing a reagent such as carbonyl diimidazole and then coupled with the appropriate amine, $Y(CH_2)_nNH_2$, to provide the amides 2. The amides 2 were then treated with the sodium salt of the desired isotope of iodine, NaI*, in For the preparation of the amides 2 wherein $R^1=CO_2H$ it often is advantageous to perform the coupling reaction (Scheme I, 1→2) on an appropriate ester of 1 (1; wherein $R^1=CO_2Me$, $CO_2t$-Bu, etc.) followed by hydrolysis of the ester group employing chemistry well known to one skilled in the art.

Finally, the phthalamic acid derivatives of 2 (X=NHCO, $R^1=CO_2H$) are generally best prepared employing the route shown in Scheme II. In this case the acid 3 is converted to the amide 4 by standard chemistry. The nitro group of 4 is then reduced with iron powder in acetic acid to afford the aniline 5, followed by the condensation of 5 with phthalic anhydride to provide the required analog of 2.

SCHEME II

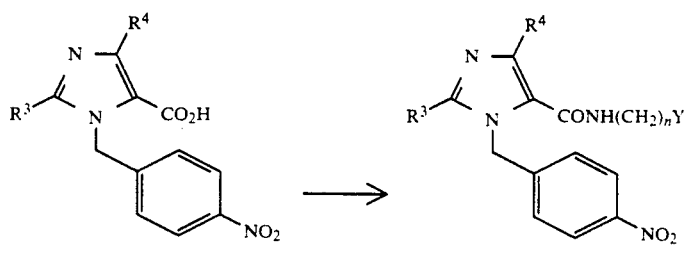

SCHEME II

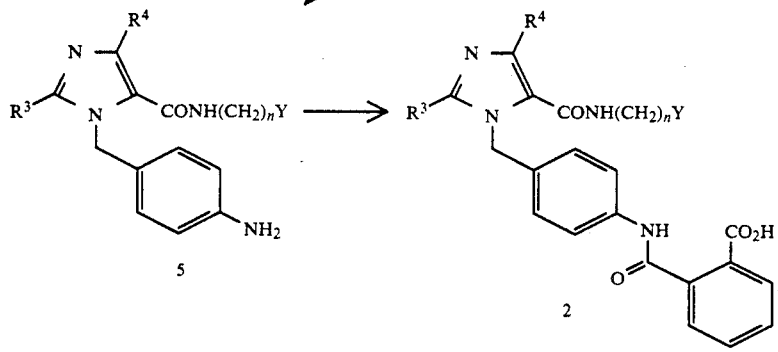

The following working examples will further illustrate the invention.

EXAMPLE 1

Part A

Preparation of 4-Chloro-N-[2-(4-hydroxyphenyl)ethyl]-2-propyl-1-[[2'-(tetrazol-5-yl)biphenyl-4-yl]methyl]-imidazole-5-carboxamide To a solution of 4.86 g of 4-chloro-2-propyl-1-[[2'-(tetrazol-5-yl)biphenyl-4-yl]methyl]imidazole-5-carboxylic acid in 115 mL of tetrahydrofuran at 25° C. is added 2.25 g of carbonyl diimidazole, and the resulting solution is stirred at 25° C. for 3 hours. To the solution is added 3.94 g of tyramine and 23 mL of 2-propanol, and the mixture was stirred at 25° C. for an additional 3 hours. The reaction mixture is poured into water, and the resulting emulsion is adjusted to pH 3 employing hydrochloric acid and then extracted with chloroform. The combined extracts are washed with water and brine, dried over anhydrous sodium sulfate, and concentrated. Column chromatography (elution: 10% 2-propanol/chloroform) affords 3.15 g of the product as an amorphous solid. NMR (300 MHz, DMSO-d$_6$) δ 8.07 (t, 1H, J=8 Hz), 7.69−7.50 (m, 4H), 7.07−6.99 (m, 6H), 6.65 (d, 2H, J=8 Hz), 5.42 (s, 2H), 3.36 (quart., 2H, J=7 Hz), 2.63 (t, 2H, J=7 Hz), 2.50 (t, 2H, J=7 Hz), 1.51 (sext., 2H, J=7 Hz), 0.82 (t, 3H, J=7 Hz).

The following compounds can be prepared by the procedure of Example 1, Part A or by the modified procedures described in the specifications.

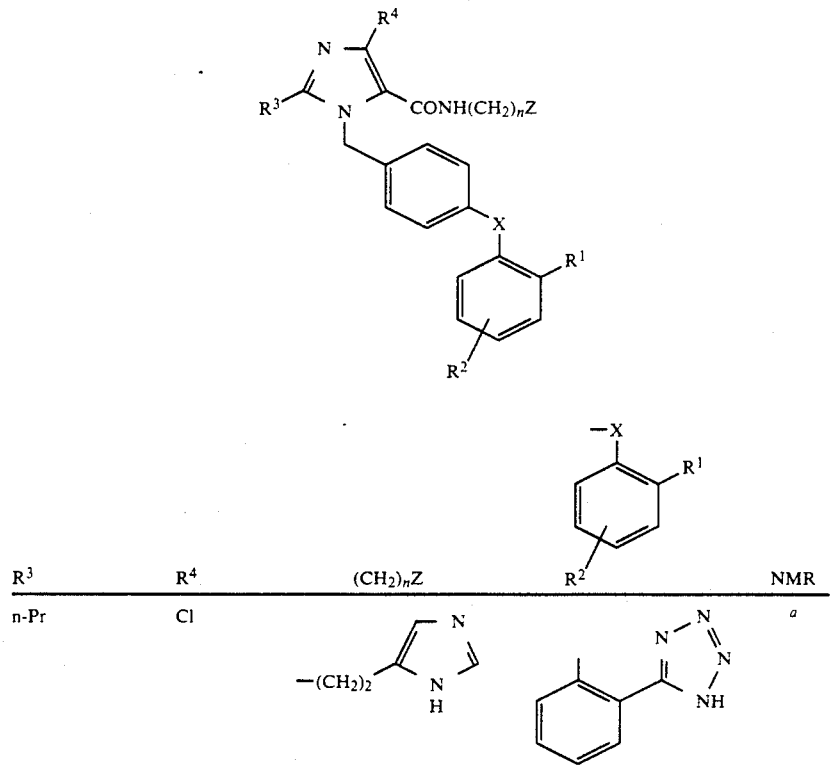

| R$^3$ | R$^4$ | (CH$_2$)$_n$Z | R$^2$ | NMR |
|---|---|---|---|---|
| n-Pr | Cl | —(CH$_2$)$_2$-(imidazole) | (tetrazole) | a |

-continued
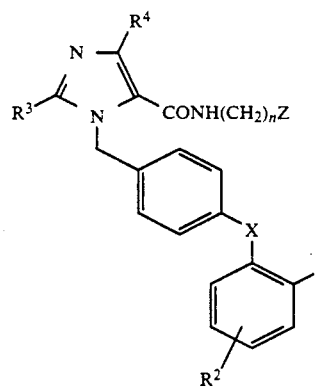
| R³ | R⁴ | (CH₂)ₙZ | 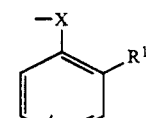 R² | NMR |
|---|---|---|---|---|
| n-Bu | Cl | —(CH₂)₂—⌬—OH | —NH—C(O)— phenyl-CO₂H | |
| n-Pr | CF₃ | —CH₂—⌬—OH | tolyl-tetrazole | |
| n-Bu | Me | —CH₂—⌬—OH | tolyl-SO₃H | |
| n-Pr | Et | —(CH₂)₂—⌬—OH | tolyl-tetrazole | |
| n-Bu | H | —(CH₂)₂—imidazole | —NH—C(O)— CH₃-phenyl-CO₂H | |
| n-Pr | CF₃CF₂ | —(CH₂)₂—⌬—OH | C(O)-phenyl-CO₂H | |

-continued

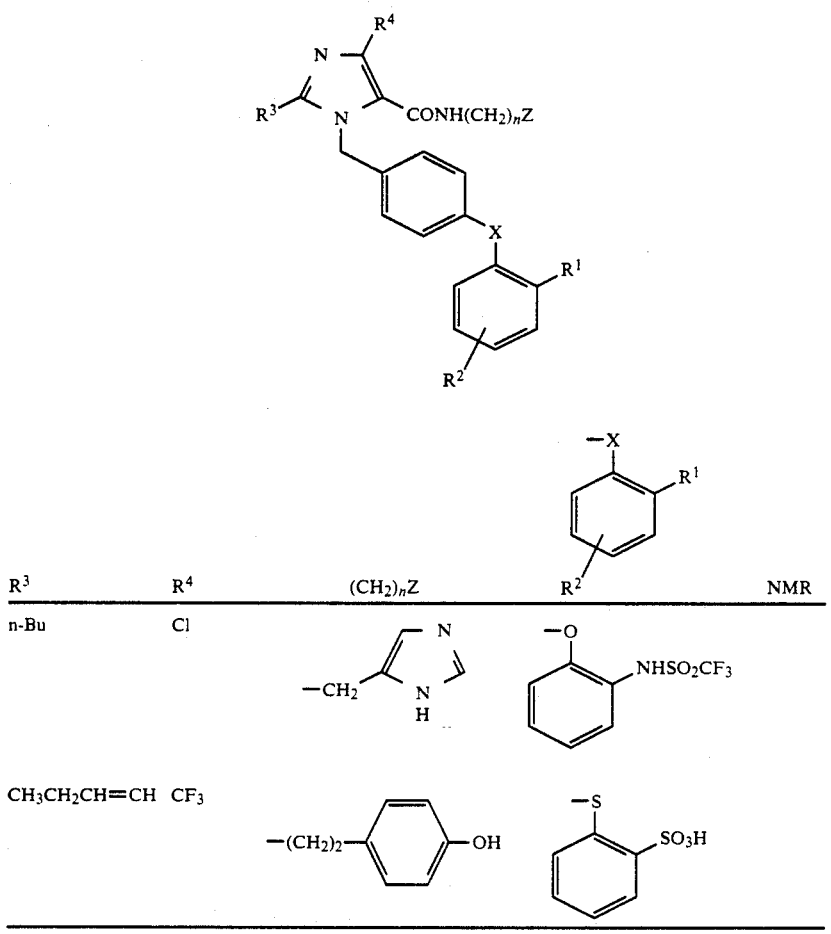

<sup>a</sup>NMR(300 MHz, DMSO-d₆)δ8.24(t, 1H, J=7Hz), 8.17(s, 1H), 7.68(d, 1H, J=8Hz), 7.55-7.40(m, 3H), 7.03(d, 2H, J=8Hz), 6.83(m, 3H), 5.40(s, 2H), 3.51(quart., 2H, J=7Hz), 2.74(t, 2H, J=7Hz), 2.50(t, 2H, J=7Hz), 1.54(sext., 2H, J=7Hz), 0.83(t, 3H, J=7Hz).

Part B

Preparation of 4-Chloro-N-[2-[4-hydroxy-3-(iodo-125I)-phenyl]ethyl]-2-propyl-1-[[2'-(tetrazol-5-yl)biphenyl-4-yl]methyl]imidazole-5-carboxamide In a combi-v-vial is dispensed 10.5 mCi of commercially available sodium iodide [125I]. To this is added 100 ml of 50 mM sodium phosphate pH 7.4, followed by 50 mg of 4-Chloro-N-[2-(4-hydroxyphenyl)ethyl]-2-propyl-1-[[2'-(tetrazol-5-yl)biphenyl-4-yl]methyl]-imidazole-5-carboxamide in 50 mL of absolute ethanol. The reaction is initiated by the addition of 50 mg of chloramine-T in 50 mL of deionized water. The reaction is allowed to proceed for one minute whereupon 50 mg of sodium meta-bisulfite in 50 mL of deionized water is added to quench.

Purification takes place on a analytical uBondapak C-18 RP column (Waters) using Waters Model 501 pumps and a Waters Model 680 Automated Gradient Controller. UV detection is performed using a Spectroflow Model 757 UV detector (Kratos), and UV detection is set at 254 nm. Radiochemical detection is done using a NICO GM tube. A gradient is run from 20% methanol/water to 80% methanol/water over 45 minutes at 1 mL/min. After reaction, the sample is immediately injected onto the pre-equilibrated system. The desired product elutes at approximately 28 minutes into the run and affords 6 mCi (57%) radiochemical yield. The hot [125I] product is characterized by its HPLC retention time, which is identical to that of a sample of the cold [129I] product. NMR (300 MHz, DMSO-d₆) of the cold [129I] product: δ 10.09 (br s, 1H), 8.04 (t, 1H, J=8 Hz), 7.69−7.63 (m, 2H), 7.58−7.49 (m, 3H), 7.02 (m, 5H), 6.77 (d, 1H, J=8 Hz), 5.41 (s, 2H), 3.35 (m, 2H), 2.63 (t, 2H, J=7 Hz), 2.49 (t, 2H, J=7 Hz), 1.50 (sext., 2H, J=7 Hz), 0.83 (t, 3H, J=7 Hz).

Table 1 illustrates compounds which can be prepared from the appropriate non-iodinated precursors by the method of Example 1, Part B.

TABLE 1
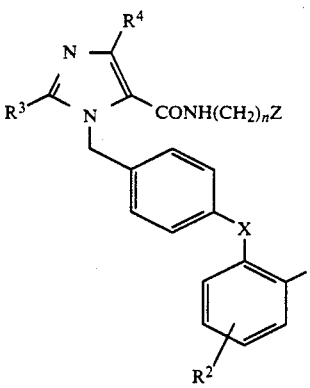
| Example | R³ | R⁴ | (CH₂)ₙZ | −X−⟨R¹,R²⟩ |
|---|---|---|---|---|
| 2 | n-Pr | Cl | 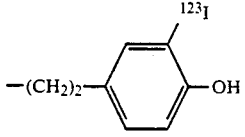 | 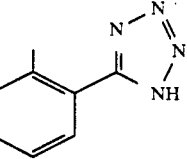 |
| 3 | n-Pr | Cl | 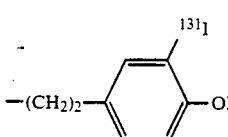 | 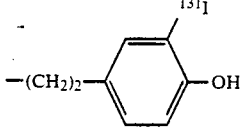 |
| 4 | n-Pr | Cl | 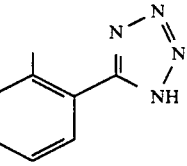 | 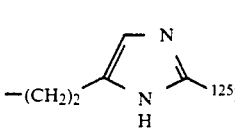 |
| 5 | n-Bu | Cl | 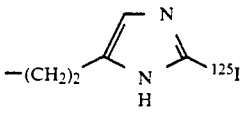 | 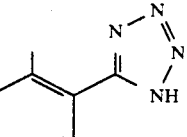 |
| 6 | n-pr | CF₃ | 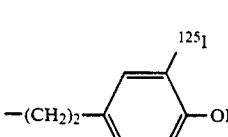 | 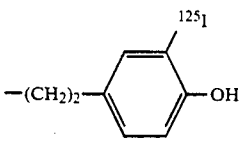 |
| 7 | n-Bu | Me | 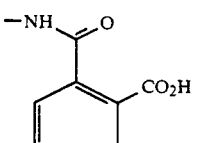 | 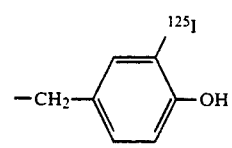 |

TABLE 1-continued

General structure:

R³—C(=N)—N(—R⁴)...imidazole with CONH(CH₂)ₙZ substituent, N-CH₂-phenyl-X-phenyl(R¹)(R²)

| Example | R³ | R⁴ | (CH₂)ₙZ | —X—phenyl(R¹,R²) |
|---|---|---|---|---|
| 8 | n-Pr | Et | —(CH₂)₂—(2-$^{125}$I, 4-OH-phenyl) | 2-(tetrazol-5-yl)phenyl |
| 9 | n-Bu | H | —(CH₂)₂—(4-$^{125}$I-imidazol-5-yl) | —NH—C(=O)—(2-CH₃, 6-CO₂H-phenyl) |
| 10 | n-Pr | CF₃CF₂ | —(CH₂)₂—(2-$^{125}$I, 4-OH-phenyl) | 2-(acetyl), 6-CO₂H-phenyl (via direct bond) |
| 11 | n-Bu | Cl | —CH₂—(4-$^{125}$I-imidazol-5-yl) | —O—(2-NHSO₂CF₃-phenyl) |
| 12 | CH₃CH₂CH=CH | CF₃ | —(CH₂)₂—(2-$^{125}$I, 4-OH-phenyl) | —S—(2-SO₃H-phenyl) |

UTILITY

The compounds of the invention have utility as research tools in studying receptors such as AT₁ even in the presence of AT₂ and other receptors. More specifically, these compounds are useful for the following in vivo or in vitro studies: (a) detecting AT₁ receptors; (b) measuring the number of receptors on a cell or in a sample; (c) determining the efficiency of the receptor for receiving a chemical signal; (d) following the speed and details of the signalling process; (e) searching for receptor agonists or antagonists either competitively or cooperatively; (f) autoradiographic determinations; (g) tissue distribution determinations; and (h) identifying new receptor functions.

The prior art describes methods and procedures for conducting the above studies and makes obvious to those skilled in the art how the radioligand compounds of this invention can be used in the studies to achieve the desired determinations. For example, studies (a) through (e) are described in McQueen & Sample, Methods in Neurosciences, Vol. 5, pp. 312-330 (1991) and in Peach & Levens, Adv. Exp. Med. 130, pp. 171-194 (1980). Studies (a), (b), (d) and (e) are described in Chiu et al., Biochemical and Biophysical Research Communications (BBRC) 172, pp. 1195-1202 (1990).

The compounds of this invention can be substituted for the radioligand, tritiated DuP 753, used in the studies described in this reference.

Study (f) is described in BBRC 165, pp. 196-203 (1989). Study (g) is described in W. McNally et al., Pharmaceutical Research 6, pp. 924-930 (1989), and L. A. Stevens et al., Arzeneim. Forsch, Drug Res. 34, pp. 1723-1729 (1984). Study (h) is described in V. DeNoble et al., Brain Research, 561:230-235 (1991).

All the above prior art references describing one or more of the studies (a) through (h) are incorporated herein by reference for a more complete understanding of how the compounds of this invention are useful as radioligands for in vivo or in vitro studies.

What is claimed is:

1. A novel compound of the formula

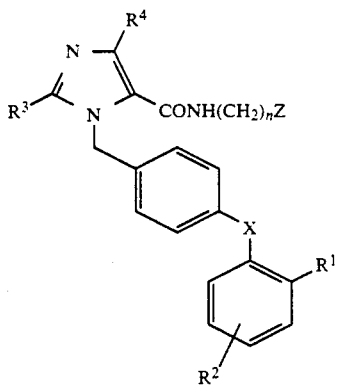

(I)

wherein
$R^1$ is $CO_2H$; $NHSO_2CF_3$; $SO_3H$; or

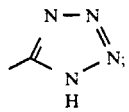

$R^2$ is H, alkyl of 1 to 4 carbon atoms, halogen, or alkoxy of 1 to 4 carbon atoms;
$R^3$ is alkyl, alkenyl, or alkynyl of 2 to 7 carbon atoms;
$R^4$ is H, Cl, Br, I; alkyl of 1 to 4 carbon atoms; $C_vF_{2v+1}$, where $v=1-3$;
X is a carbon-carbon single bond, —CO—, —O—, —S—, or —CONH—;
Z is

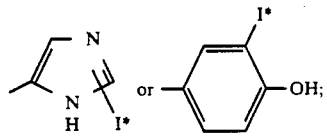

I* is I-123, I-125, or I-131; and
n is 1-3.

2. A compound of claim 1 wherein
$R^1$ is

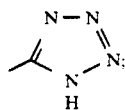

$R^2$ is H; and
X is a carbon-carbon single bond.

3. The compound of claim 2 which is 4-chloro-N-[2-[4-hydroxy-3-(iodo-125I)phenyl]ethyl]-2-propyl-1-[[2'-(tetrazol-5-yl)biphenyl-4-yl]methyl]imidazole-5-carboxamide.

4. The compound of claim 2 which is 4-chloro-N-[2-[4-hydroxy-3-(iodo-123I)phenyl]ethyl]-2-propyl-1-[[2'-(tetrazol-5-yl)biphenyl-4-yl]methyl]imidazole-5-carboxamide.

5. The compound of claim 2 which is 4-chloro-N-[2-[4-hydroxy-3-(iodo-131I)phenyl]ethyl]-2-propyl-1-[[2'-(tetrazol-5-yl)biphenyl-4-yl]methyl]imidazole-5-carboxamide.

6. The compound of claim 2 which is 4-ethyl-N-[2-[4-hydroxy-3-(iodo-125I)phenyl]ethyl]-2-propyl-1-[[2'-(tetrazol-5-yl)biphenyl-4-yl]methyl]imidazole-5-carboxamide.

7. The compound of claim 2 which is 4-chloro-N-[2-[2-(iodo-125I)imidazol-4(5)-yl]ethyl]-2-propyl-1-[[2'-(tetrazol-5-yl)biphenyl-4-yl]methyl]imidazole-5-carboxamide.

* * * * *